United States Patent [19]

Kanoh et al.

[11] Patent Number: 4,975,422
[45] Date of Patent: Dec. 4, 1990

[54] ANGIOGENESIS INHIBITOR

[75] Inventors: Tamotsu Kanoh, Chiba; Kenichi Matsunaga, Tokorozawa; Kenichi Saito; Takayoshi Fujii, both of Tokyo, all of Japan

[73] Assignee: Kureha Kagaku Kogyo Kabushiki Kaisha, Tokyo, Japan

[21] Appl. No.: 368,232

[22] Filed: Jun. 19, 1989

[30] Foreign Application Priority Data

Jun. 30, 1988 [JP] Japan ............................. 63-163065

[51] Int. Cl.$^5$ ........................ A61K 31/715; C02H 1/00
[52] U.S. Cl. ...................................... 514/54; 536/1.1; 536/55.1; 536/123
[58] Field of Search .................. 514/54; 536/1.1, 55.1, 536/123

[56] References Cited

U.S. PATENT DOCUMENTS

| | | | |
|---|---|---|---|
| 4,182,753 | 1/1980 | Saltarelli | 424/115 |
| 4,202,885 | 5/1980 | Asano et al. | 536/55.1 |
| 4,202,966 | 5/1980 | Misaki et al. | 536/1.1 |
| 4,202,969 | 5/1980 | Ueno et al. | 536/55.1 |
| 4,229,570 | 10/1980 | Ueno et al. | 536/55.1 |
| 4,614,733 | 9/1986 | Yoshikumi et al. | 536/55.1 |

OTHER PUBLICATIONS

Patent Abstracts of Japan, vol. 10, No. 287 (C-375) [2343], Sep. 30, 1986.
Dialog Information Services, file 159, Cancerlit 63-89, Accesion No. 0108234, Kubota, "Experimental Chemotherapy of Carcinomas of the . . . ".

*Primary Examiner*—Ronald W. Griffin
*Assistant Examiner*—Pamela S. Webber
*Attorney, Agent, or Firm*—Nixon & Vanderhye

[57] ABSTRACT

The present invention discloses an angiogenesis inhibitor containing as an active ingredient protein-polysaccharides produced by extraction of mycelia or fruit bodies obtained from culture of a Basidiomycete belonging to a genus Coriolus.

The protein-polysaccharide contains about 18 to about 38% by weight of protein, being free from protein-polysaccharides having molecular weight of less than 5,000.

More in detail, said protein-polysaccharides of the present invention contain 3 to 6% of nitrogen, a polysaccharide portion thereof, as the main fraction, is composed of $\beta$-D-glucan and this glucan portion has branched structures containing 1→3, 1→4 and 1→6 bonds, wherein the protein-component amino acids are mostly acidic amino acids of aspartic acid and glutamic acid, and neutral amino acids of valine and leucine, while the basic amino acids of lysine and alginine are small in content, and the protein-polysaccharide is soluble in water but hardly soluble in methanol, pyridine, chloroform, benzene and hexane and starts to be gradually decomposed at about 120° C.

13 Claims, No Drawings

ANGIOGENESIS INHIBITOR

BACKGROUND OF THE INVENTION

The present invention relates to an angiogenesis inhibitor containing as an active ingredient a protein-polysaccharide produced by extraction of mycelia or fruit bodies obtained from culture of a basidiomycete belonging to the genus Coriolus.

Blood vessels play very important roles in a biological field for living bodies, especially for animals having closed-cycle blood vessel system, for example, transporting nutrients to and taking away waste substances from tissues and/or organs in the bodies, which roles are indispensable to maintain the life of the bodies.

Accordingly, variety of researches relating to new formation of blood vessels, maintenance and improvement of their function etc. have been pursued so far subjecting the patients of suffering from high blood pressure, ischemic diseases, etc.

On the other hand, it has been gradually become clear that blood vessels playing such important roles which are essential to living bodies, sometimes extraordinarily proliferate and such proliferation induces several illness or makes some diseases worse. For example, recently it becomes known that certain percentage of patients of diabetes have unusual proliferation of capillary vessels in lens of eyeball and the patients occasionally become blind.

Further, when it comes to cancer diseases, which become top of the death causes in Japan, it is also known that capillary vessels of the host proliferate extraordinarily to the direction of cancer. [J. Folkman, page 85 to 97, SCIENTIFIC AMERICAN (Japanese Edition) Special Edition for Cancer, published by NIKKEI Science Co. on November 1981].

If there were no such unusual proliferation of blood vessels in a host, even if there existed a primary tumor, the tumor would not be able to grow to the size of more than several mm in its diameter and the host would not have any fatal symptom induced by such primary tumor. Accordingly, if one could inhibit or prevent such blood vessels proliferation, it becomes possible to prevent or cure several diseases induced by the proliferation.

So far, there have been known the substances having angiogenesis inhibiting activity such as anti-inflammatory medicines disclosed in Japanese Patent Application Laid-Open (KOKAI) 61-106,521 (1986) and Protamin disclosed in "Nature, vol. 297, pages 307 to 312 (1982)". However, both substances have some problems in view of their administration for a long period.

As a nature of this kind of medicines, it is necessary to administer for a long period, since the medicines become much less effective after capillary vessels have once reached to eye-lens or tumor and furthermore it is practically impossible to know in advance when the vessels start to proliferate. Therefore, to have safe medicines having substantially no side effect is extremely important.

The present inventors have extensively studied to find a substance which has angiogenesis inhibiting activity and which is extremely safe. As the result of their efforts, the present invention has been achieved.

SUMMARY OF THE INVENTION

In an aspect of the present invention, there is provided an angiogenesis inhibitor containing as an active ingredient protein-polysaccharides produced by extraction of mycelia or fruit bodies obtained from culture of a Basidiomycete belonging to a genus Coriolus, said protein-polysaccharide containing about 18 to about 38% by weight of protein and being free from protein-polysaccharides having molecular weight of less than 5,000.

In another aspect of the present invention, there is provided an angiogenesis inhibitor containing as an active ingredient the protein-polysaccharide containing 3 to 6% of nitrogen, a polysaccharide portion thereof, as the main fraction, is composed of $\beta$-D-glucan and this glucan portion has branched structures containing 1→3, 1→4 and 1→6 bonds, wherein the protein-component amino acids are mostly acidic amino acids of aspartic acid and glutamic acid, and neutral amino acids of valine and leucine, while the basic amino acids of lysine and arginine are small in content, the protein-polysaccharide is soluble in water but hardly soluble in methanol, pyridine, chloroform, benzene and hexane and starts to be gradually decomposed at about 120° C.

DETAILED DESCRIPTION OF THE INVENTION

The present invention relates to an angiogenesis inhibitor containing as an active ingredient protein-polysaccharides produced by extraction of mycelia or fruit bodies obtained from culture of a Basidiomycete belonging to a genus Coriolus, said protein-polysaccharide containing about 18 to about 38% by weight of protein, being free from protein-polysaccharide of which molecular weight is less than 5,000, containing 3 to 6% of nitrogen, a polysaccharide portion thereof, as the main fraction, is composed of $\beta$-D-glucan and this glucan portion has branched structures containing 1→3, 1→4 and 1→6 bonds, wherein the protein-component amino acids are mostly acidic amino acids of aspartic acid and glutamic acid, and neutral amino acids of valine and leucine, while the basic amino acids of lysine and arginine are small in content, the protein-polysaccharide is soluble in water but hardly soluble in methanol, pyridine, chloroform, benzene and hexane and starts to be gradually decomposed at about 120° C.

The protein-polysaccharides used as an active ingredient of a pharmaceutical composition to inhibit angiogenesis according to the present invention are the substance obtainable by the methods disclosed in the prior patents such as Japanese Patent Publication Nos. 51-36,322 (1976), 56-14,274 (1981) (corresponding to U.S. Pat. No. 4,202,969), 56-14,276 (1981) (corresponding to U.S. Pat. No. 4,140,578) and 56-39,288 (1981) (corresponding to U.S. Pat. No. 4,268,505) and U.S. Pat. No. 4,051,314. Such protein-polysaccharides can be obtained by an extraction of a cultured broth of a mycelium or fruit body of a basidiomycete belonging to the genus Coriolus with a hot water or an aqueous alkaline solution. The protein-polysaccharides contain about 18 to 38% by weight of protein and have a molecular weight of not less than 5,000, preferably 5,000 to 300,000 (as measured by ultracentrifugal analysis).

Shown below are some examples of protein-polysaccharides disclosed in the art, which can also be used as one of angiogenesis inhibitors of the present invention.

A protein-polysaccharide, which is in the form of a hydrolysate, gives positive results in ninhydrin, anisaldehyde, molisch, anthrone, tryptophane-sulfonic acid, chromo-tropic acid-sulfuric acid, carbazole cysteinesulfonic acid, aniline-hydrochloric acid, resorcinol-hydrochloric acid, tollens and thioglycol-sulfuric acid reactions but negative results in ferric chloride and fehling reactions, said protein-polysaccharide being produced by the process comprising forming a culture medium or a liquid extract of mycelium of a species of fungi belonging to the class Basidiomycetes and selected from the group consisting of *Coriolus versicolor, Coriolus conchifer, Coriolus pargamenus, Coriolus hirsutus, Coriolus biformis, Coriolus consors* and *Coriolus pubescens*, and separating or liquid-extracting the protein-polysaccharide from said culture medium. (Refer to U.S. Pat. No. 4,051,314).

A protein-polysaccharide produced by extracting a fungus of the genus Coriolus of the Polyporaceae family of class Basidiomycetes selected from the group consisting of *Coriolus biformis, Coriolus conchifer, Coriolus consors, Coriolus hirsutus, Coriolus pargamenus, Coriolus pubescens* and *Coriolus versicolor* with an aqueous solvent under pressure at a temperature within the range of 150° C. to 200° C. to obtain an extract containing the protein-polysaccharide; refining said extract to remove substances having a molecular weight less than 5,000 and separating the protein-polysaccharide from said extract. (Refer to U.S. Pat. No. 4,202,885).

A protein-polysaccharide produced by (a) extracting *Coriolus versicolor* (Fr.) Quèl. with an aqueous alkaline solution having a concentration within the range of from 0.01 to 2.0N at a temperature of 50° to 100° C.; (b) neutralizing the resultant extract and including an alkaline salt therewith at a concentration of at least 0.4 M/l, whereby the molecular shape of said protein-polysaccharide is rendered more spherical; and (c) subjecting the spherically modified protein-polysaccharide to ultrafiltration through a membrane as a molecular sieve under a pressure of at least 0.5 kg/cm$^2$, whereby portions of the mixture having a molecular weight of less than 5,000 are removed therefrom. (Refer to U.S. Pat. No. 4,202,969).

A protein-polysaccharide substantially free from units having a molecular weight below about 5,000, produced by extracting a fungus of the genus Coriolus of the family Polyporaceae of the class Basidiomycetes at a temperature of 50° to 100° C. wherein:

(a) a first extraction step is conducted with water or a dilute aqueous alkaline solution;

(b) a second extraction step is conducted in an alkaline medium having a normality higher than said first extraction step and below about 2.0; and (c) a third extraction step is conducted at a normality higher than said second extracting step and below about 2.0. (Refer to U.S. Pat. No. 4,229,570).

The protein-polysaccharide according to the present invention (hereinafter referred to as "the present substance") is very low in its toxicity and produces almost no harmful side effect and therefore is very safe to the living organisms. The acute toxicity of the present substance is shown in Table 1 below.

TABLE 1

| Animal Tested | Route of Administration | LD$_{50}$(mg/kg) Female | LD$_{50}$(mg/kg) Male |
| --- | --- | --- | --- |
| Mouse | Intravenous | >1,300 | >1,300 |
| Mouse | Subcutaneous | >5,000 | >5,000 |
| Mouse | Intraperitoneal | >5,000 | >5,000 |
| Mouse | Oral | >20,000 | >20,000 |
| Rat | Intravenous | >600 | >600 |
| Rat | Subcutaneous | >5,000 | >5,000 |
| Rat | Intraperitoneal | >5,000 | >5,000 |
| Rat | Oral | >20,000 | >20,000 |

The acute toxicity shown above was determined by the following test method.

Used as test animals were ICR-JCL strain mice which were 4 to 5 weeks old and weighed 21 to 24 g and Donryu strain rats which were 4 to 5 weeks old and weighed 100 to 150 g. The present substance was dissolved in a physiological saline solution and administered to the test animals through four routes: intravenous, subcutaneous, intraperitoneal and oral. The general symptoms, death and body weight of each test animal were observed over a period of 7 days and after the end of this observation period, each test animal was killed and anatomized.

As seen from the Table 1, there was caused no death of rats and mice even when they were given the maximum amount of dosage of the present substance possible to take, and it was practically impossible to determine the LD$_{50}$ value. This indicates such a high level of safety of the present substance for the living organism. As seen from the above, the present substance is very low in acute toxicity and useful as an angiogenesis inhibitor. Further, taking into account of the facts that LD$_{50}$ values of indomethacin, which is most popular anti-inflammatory drug, and of Protamin are 50 mg/kg (oral) and 100 mg/kg (intravenous), respectively, it is very clear that the present substance is very safe.

In use of the present substance as an angiogenesis inhibitor, the present substance can be worked into any desired form of pharmaceutical composition and the composition can be administered in any desired way, either oral or parenteral.

In the case of oral administration, the preparation may take the form of tablet, granules, powder, capsule or the like, which may contain in its composition carrier or adjuvant generally used for the pharmaceutical composition, such as binder, inclusion, excipient, lubricant, disintegrator, wetting agent, etc.

PHARMACOLOGICAL FEATURES OF THE PRESENT SUBSTANCE

Next, the physiological features of the present substance are described. The present substance has an activity to inhibit angiogenesis. When this activity was investigated according to the method described in "IGAKU NO AYUMI (Progress in Medicine) vol. 122, page 890 (1982)", it was recognized that the substance had an activity to inhibit a proliferation of blood vessels induced by an experimental animal tumor in a living body.

On the other hand, a proliferation of blood vessels in a living body can also be recognized by knowing an activity of alkalinephosphatase which can be measured by dying alkalinephosphatase. [Refer to NICHIGAN KAISHI (J. of Japanese Eye Society), vol. 86 (10), page 163 to 173 (1982)]. According to the Journal, the low activity of the enzyme means low proliferation of the vessels and vice versa.

The inhibiting function of the present substance was recognized by measuring an activity of alkalinephosphatase produced by endotherial cells of blood vessels.

The same activity was also recognized against a diabetic retinopathy.

In use of the present substance as an angiogenesis inhibitor, the present substance can be worked into any desired form of preparation (pharmaceutical composition). Also, the preparation can be administered in any desired way, either oral or parenteral.

In the case of oral administration, the preparation may take the form of tablet, granule, powder, capsule or the like, which may contain in its composition carrier(s) or adjuvant(s) generally used for the pharmaceutical composition, such as binder, inclusion, excipient, lubricant, disintegrator, wetting agent, etc. When used as an oral liquid preparation, the composition of the present invention may be worked into a liquid for internal use, shake mixture, suspension, emulsion, syrup or the like. Also, the composition of the present invention may take the form of a dry product which is made into a solution when used. Such liquid preparations may contain generally used types of additive and/or preservative.

In the case of injection, the composition of the present invention may contain such additives as stabilizer, buffering agent, preservative agent and the like, and the preparation may be offered in the form of unit dosage ampule or in the multiple-dosage containers. The composition of the present invention may be worked into the form of aqueous solution, suspension, solution or emulsion in an oily or aqueous vehicle. The present substance as the active ingredient may be in the form of powder which is redissolved in a suitable vehicle, such as pyrogen-free sterilized water, before use.

The angiogenesis inhibitor of the present invention is administered to human and animal either orally or parenterally. Sublingual administration is included in the form of oral administration. The form of the parenteral administration includes injection such as subcutaneous, intramuscular and intravenous injection and instillation.

The dosage of the angiogenesis inhibitor of the present invention is variable depending on whether the subject is human or animal and according to such factors as age, individual difference, condition of the disease etc., but usually when the subject is human, the oral dosage of the present substance is 10 to 1,000 mg, preferably 20 to 600 mg per 1 kg of body weight and per day and this amount of the present substance can be given one to three times a day divided into an equal portion by weight.

The present substance is a pharmaceutical which is extremely high in safety and efficacious to inhibit angiogenesis.

The present invention will hereinafter be described more particularly with reference to the examples thereof, however the examples are merely intended to be illustrative and not to be construed as limiting the scope of the invention.

EXAMPLE 1

Preparation of The Protein-Polysaccharides of The Present Invention 150 g of dried and pulverized mycelia of *Coriolus versicolor* (Fr.) Quél. (FERM-P No. 2412) were introduced into 3-liter stainless steel tank with 2000 ml of water at the temperature of 93° to 98° C., stirred for 3 hours and then cooled to room temperature. The resulted slurry was separated into an extract (referred to as "extract A") and a residue by centrifugation. The residue was further extracted with 2,000 ml of 0.4N of aqueous solution of NaOH at the temperature of 90° to 95° C. for 3 hours and cooled to room temperature. pH value of the slurry obtained was adjusted to 7.0 by 2N aqueous solution of HCl and separated into an extract (referred to as "extract B") and a residue by centrifugation.

The extracts A and B were combined and concentrated to 400 ml by vacuum distillation device and then lower molecular weight substances were removed by ultrafilter (HFG: Manufactured by Dow Chemical Co.) and freeze dried. 28.6 g of dried protein-polysaccharides were obtained.

EXAMPLE 2

Inhibition of Abnormal Proliferation of ICR Mouse Blood Vessels Induced by Salcoma-180.

$5 \times 10^6$ of Salcoma-180 calcinoma cells were sealed into Millipore diffusion chamber (PR000/401, manufactured by Millipore Japan Co.), and the chamber was implanted onto the dorsal fascia of ICR mice of 8 weeks age. The proliferation of blood vessels of host mice induced by the calcinoma cells was studied 9 days after the implant and observed abnormal proliferation of the vessels. [Refer to "IGAKU NO AYUMI (Progress in Medicine), vol. 122, page 890 (1982)].

On the other hand, to the implanted mice the protein-polysaccharide, prepared in Example 1, was orally administered in a dosage of 0.5 g/kg of body weight/day in a form of 10% physiological saline solution. at 3rd, 5th and 8th days after the implantation and studied a proliferation of the vessels on 9th day after the implantation. In those mice administered the protein-polysaccharide, substantially no abnormal proliferation was observed, namely, the inhibition activity of the present substance was recognized.

Those inhibiting activity of the present substance was confirmed quantitatively by measuring an activity of alkalinephosphatase produced by endotherial cells of blood vessels in a homogenized tissue samples taken from the dorsal fascia 9 days after the implantation. Results are shown in Table 2 below.

TABLE 2

|  | Alkalinephosphatase Activity (Unit/μg protein × $10^3$) |
|---|---|
| Polysaccharide Group | 38 |
| Control Group | 135 |

EXAMPLE 3

Inhibition of Abnormal Proliferation of BDF$_1$ Mouse Blood Vessels Induced by Lewis Lung Cancer Cells.

$10^6$ of Lewis lung cancer cells were inoculated subcutaneously into BDF$_1$ mice and their proliferation of blood vessels was studied in the same manner as in Example 2 for two groups, one group was orally administered with 0.5 g/kg of body weight/day of a protein-polysaccharide obtained by the same method described in Example 1 (referred to as "tested group") and the other group was without an administration of the protein-polysaccharide (referred to as "control group").

The inhibiting effect against the proliferation was observed in the tested group and lower activity of alkalinephosphatase was also observed for the tested group, of which results are shown in Table 3, quantitatively.

TABLE 3

| | Alkalinephosphatase Activity (Unit/μg protein × 10³) |
|---|---|
| Tested Group | 32 |
| Control Group | 117 |

EXAMPLE 4

Effect of a protein-polysaccharide to Wistar rats suffering from abnormal proliferation of blood vessels induced by diabetic retinopathy exeprimentally caused.

65 mg/kg of body weight of streptozotosin were injected to male Wistar rats of 5 week age via tail vein and after around 3 months of the injection 3,3'-iminodipropionitrile was administered to the rats trying to induce an experimental diabetic retinopathy. Several rats among the ones administered with 3,3'-iminodipropionitrile started to have an abnormal proliferation of capillary vessels in their eye lenses of which symptom was just like retinitis proliferans. The rats starting this symptom were divided into two groups and one group was kept without further treatment as control group and the other group was orally administered 0.3 g/kg of body weight/day of the protein-polysaccharide prepared in the same manner as in Example 1. for 7 days starting from next day of the day administered iminodipropionitrile as tested group. In the tested group, inhibition of the vessels in the lens was observed and this inhibiting effect was confirmed by measuring activity of alkalinephosphatase produced by endotherial cells in a test samples of the lens prepared in the same manner as in Example 2. The results of the measurement were shown in Table 4.

TABLE 4

| | Alkalinephosphatase Activity (Unit/μg protein × 10³) |
|---|---|
| Tested Group | 1 |
| Control Group | 8 |

EXAMPLE 5

Effect of a protein-polysaccharide to Wistar rats suffering from abnormal proliferation of blood vessels induced by experimental prematurity retinopathy.

Palpebrae of Wistar rats were carefully cleavaged at three days after their birth and breeded in a chamber containing an atomosphere having oxygen in high concentration. Several rats among the ones breeded in the chamber started to have a symptom of experimental prematurity retinopathy. The rats starting this symptom were divided into two groups and one group was kept without further treatment as control group and the other group was orally administered 0.5 g/kg of body weight/day of the protein-polysaccharide prepared in the same manner as in Example 1. for 7 days starting from next day of the division as tested group. In the tested group, inhibition of the proliferation of the vessels was observed and this inhibiting effect was confirmed by measuring activity of alkalinephosphatase produced by endotherial cells in a test samples of the lens prepared in the same manner as in Example 2. The results of the measurement were shown in Table 5.

TABLE 5

| | Alkalinephosphatase Activity (Unit/μg protein × 10³) |
|---|---|
| Tested Group | 0.5 |
| Control Group | 7 |

EXAMPLE 6

330 mg of the protein-polysaccharide prepared in the same manner as in Example 1 were put into a hard capsule (size: No. 0) by an automatic filling machine and prepared a capsule containing the inhibitor.

What is claimed is:

1. An angiogenesis inhibitor composition comprising a physiologically effective amount of a protein-polysaccharide produced by extraction of mycelia or fruit bodies obtained from culture of a basidiomycete belonging to the genus Coriolus as an active ingredient, and a pharmaceutically acceptable carrier or diluent, said protein-polysaccharide containing about 18 to 38% by weight of protein and being free from protein-polysaccharide having molecular weight of less than 5,000.

2. The angiogenesis inhibitor composition according to claim 1, wherein said protein-polysaccharide is a polysaccharide containing protein with a nitrogen content of 3 to 6%, a polysaccharide portion thereof, as the main fraction, is composed of β-D-glucan and this glucan portion has branched structures containing 1→3, 1→4 and 1→6 bonds, wherein the protein-component amino acids are mostly acidic amino acids of aspartic acid and glutamic acid, and neutral amino acids of valine and leucine, while the basic amino acids of lysine and arginine are small in content, the protein-polysaccharide is soluble in water but hardly soluble in methanol, pyridine, chloroform, benzene and hexane, and starts to be gradually decomposed at about 120° C.

3. The angiogenesis inhibitor composition according to claim 1, wherein said extraction is performed with water or an aqueous alkaline solution.

4. The angiogenesis inhibitor composition according to claim 1, wherein said extraction is performed first with water, then with an aqueous alkaline solution.

5. The angiogenesis inhibitor composition according to claim 1, wherein extracts of said extraction are purified by the method selected from the group consisting of reverse osmosis, gelfiltration, dialysis, ultrafiltration salting out and combinations thereof.

6. The angiogenesis inhibitor composition according to claim 5, wherein said purifying method contains at least a salting out.

7. The angiogenesis inhibitor composition according to claim 6, wherein said salting out is performed with ammonium sulfate.

8. A method of treating a patient suffering from neovascularization comprising administering to said patient an effective amount of the composition of a protein-polysaccharide produced by extraction of mycelia or fruit bodies obtained from culture of a basidiomycete belonging to the genus Coriolus as an active ingredient, and a pharmaceutically acceptable carrier or diluent, said protein-polysaccharide containing about 18 to 38% by weight of protein and being free from protein-polysaccharide having molecular weight of less than 5,000.

9. The method according to claim 8, wherein said neovascularization is induced by diabetic retinopathy.

10. The method according to claim 8, wherein said neovascularization is induced by prematurity retinopathy.

11. The method according to claim 8, wherein said neovascularization is induced by solid malignant tumor cells.

12. The method according to claim 8, wherein the protein-polysaccharide is administered in an amount of from 10 to 1,000 mg per kg of the patient's body weight per day.

13. The method according to claim 12, wherein the protein-polysaccharide is administered in an amount of from 20 to 600 mg per kg of the patient's body weight per day.

* * * * *